United States Patent [19]

Pontani

[11] Patent Number: 4,630,621

[45] Date of Patent: Dec. 23, 1986

[54] METHOD AND COMPOSITION FOR SIMULTANEOUSLY PERMANENTLY WAVING AND DYEING HUMAN HAIR

[76] Inventor: Susanne Pontani, P.O. Box 758, Mars, Pa. 16046

[21] Appl. No.: 781,952

[22] Filed: Sep. 27, 1985

[51] Int. Cl.⁴ .............................................. A45D 7/00
[52] U.S. Cl. ...................................................... 132/7
[58] Field of Search .............................. 132/7; 424/70

[56] References Cited

U.S. PATENT DOCUMENTS

| | | | |
|---|---|---|---|
| 2,719,104 | 9/1955 | Westerberg | 167/88 |
| 2,975,101 | 3/1961 | Charle et al. | 167/88 |
| 3,173,842 | 3/1965 | Hervey | 167/87.1 |
| 3,215,605 | 11/1965 | Soloway | 167/88 |
| 3,247,067 | 4/1966 | Miskel | 132/7 X |
| 3,368,941 | 2/1968 | Boosen | 168/88 |
| 3,396,736 | 8/1968 | Shansky | 132/7 |
| 3,399,682 | 9/1968 | Isaji | 132/7 |
| 3,399,683 | 9/1968 | Forbriger | 132/7 |
| 3,973,574 | 8/1976 | Minagawa et al. | 132/7 |
| 4,149,848 | 4/1979 | Bugaut et al. | 8/11 |
| 4,152,112 | 5/1979 | Bugaut et al. | 8/10.2 |
| 4,277,244 | 7/1981 | Bugaut et al. | 8/410 |
| 4,494,557 | 1/1985 | Nagel | 132/7 |
| 4,649,158 | 3/1972 | Kalopissis et al. | 8/10 |

*Primary Examiner*—Gregory E. McNeill
*Attorney, Agent, or Firm*—Webb, Burden, Robinson & Webb

[57] ABSTRACT

In the process of permanently waving human hair with a thioglycolic acid or other mercaptan acid solution and rebonding the hair with an oxidizing rebonding agent, the present invention is the improvement comprising contacting the hair with a dye or tint after the reforming solution has been removed from the hair but before the oxidation rebonding is complete. In addition, the improvement preferably comprises admixing a tint or dye into all or a portion of the oxidizing rebonding agent to enable the application of most or all of the rebonding agent and the tint to the hair simultaneously. The oxidizing rebonding agent containing the tint or dye is also claimed.

11 Claims, No Drawings

METHOD AND COMPOSITION FOR SIMULTANEOUSLY PERMANENTLY WAVING AND DYEING HUMAN HAIR

INTRODUCTION

In the professional hair care industry, the two most complicated and time-consuming hair treatments are the permanent waving and permanent dyeing processes. Each of these treatments requires many hours, sequential chemical applications and constant monitoring to yield good results. Not surprisingly, moreover, these two complex processes are also the most hazardous of the hair treatments, due to the application of numerous harsh chemicals in the course of each process.

Due to the well-known hazards of these treatments, therefore, hair care professionals repeatedly warn their customers that the two processes should not be performed together on the same day, or even within the same week. By contrast, the customers themselves are ordinarily eager to have both treatments completed within a single salon appointment, and furthermore frequently ask whether the two treatments might not be performed simultaneously, in order to prevent what might otherwise amount to a 3-6 hour procedure. In response to this market demand, hair care researchers and practitioners alike have endeavored to find a simultaneous "perm and tint" process which meets the demands of their customers while providing a safe and satisfactory permanent wave and tint.

BACKGROUND OF THE INVENTION

Repeated attempts have been made to wave and tint hair simultaneously by adding dye or tint to a permanent-waving ("reforming") preparation. For example, U.S. Pat. No. 3,368,941 to Boosen discloses substituted aminobenzene dyes applied to the hair in the form of a neutral to slightly alkaline cream, into which may also be added shampoos, permanent waving agents, perfumes and admixtures thereof. In addition, U.S. Pat. No. 3,399,682 to Isaji discloses the admixture of a mercaptan acid waving solution and a coal tar or certified coloring (food coloring) agent for use as a reforming solution in the ordinary permanent wave process. The dye-containing mercaptan composition is iltimately neutralized with a hydrogen peroxide or potassium bromate neutralizer.

Unfortunately, controlled tests and salon trials have consistently shown that when dyes and reforming solutions are admixed and applied to the hair, the admixture reforms the hair but does not give a satisfactory tint. More particlarly, dyes admixed with reforming solutions either yield a much lighter shade than desired, even when very high concentrations of the dye are used, or do not tint the hair at all. The reason for this failure has, moreover, gone unexplained. As a result, a widespread market demand remains for an effective method of, and composition for, simultaneously permanently waving and dyeing human hair.

BRIEF DESCRIPTION OF THE INVENTION

The present invention meets this need by providing an effective simultaneous waving and dyeing method. More particularly, in the process of permanently waving human hair with a thiglycolic acid or other mercaptan acid solution and rebonding the hair with an oxidizing rebonding agent, the present invention is the improvement comprising contacting the hair with a dye or tint after the reforming solution has been removed from the hair but before the oxidation rebonding is complete. In addition, the improvement preferably comprises admixing a tint or dye into all or a portion of the oxidizing rebonding agent to enable the application of most or all of the rebonding agent and the tint to the hair simultaneously. The oxidizing rebonding agent containing the tint or dye is also claimed.

DETAILED DESCRIPTION OF THE INVENTION

The present invention is directed to techniques of dyeing hair at the same time as permanently waving the hair by the alkaline ("cold") or acid ("warm") waving techniques. The alkaline and acid waving techniques are relatively new in the history of permanent waving, and both processes are based upon the ability of thioglycolic acid, or other mercaptan acids, to break (reduce) the sulfur bonds within the hair. Reduction of the sulfur bonds in the hair is a process called "reforming," after which the hair can be rebonded into a new configuration.

The reforming solutions or lotions used in the alkaline waving process contain thioglycolic acid, or another suitable mercaptan acid, along with ammonium hydroxide. Ordinarily, the reforming solution is applied to the hair after the hair has been wound onto permanent waving rods, although the hair may also be dampened with the reforming solution before winding, if necessary. The presence of the mercaptan acid on the hair chemically reduces the disulfide bonds of the cystine amino acid present in the keratin, and thereby chemically breaks the bonds which hold the hair in its genetically-determined straight or curly configuration. The reforming lotion is then rinsed and blotted from the hair. After removal of the reforming lotion, an oxidizing rebonding agent is applied to the hair to rebond (oxidize) the disulfide bonds into the configuration of the hair as wound onto the rods. The oxidizing rebonding agent may contain available reactive oxygen, hydrogen, peroxide, bromate, bromite or other known oxidizing compounds which are relatively nontoxic to the adjacent skin and scalp. (Because the oxidizing rebonding agent "neutralizes," or reverses, the effects of the reforming solution, oxidizing rebonding agents are often called "neutralizers.")

Acid waving is similar to the alkaline waving process. The difference between acid and alkaline reforming solutions is that alkaline waving solutions contain ammonium hydroxide or other alkali (along with the mercaptan acid) but acid waving solutions do not. Instead of the alkali available in the alkaline reforming solutions, therefore, which functions to assist penetration of the thioglycolic acid through the cuticle of the hair, the passage through the cuticle of acid reforming solutions is aided by the application of mild heat. In effect, therefore, both acid and alkaline reforming solutions are essentially the same preparations of mercaptan acid compositions, with the proviso that the alkaline reforming solution contains alkali. Because of the substantial chemical similarity of the acid and alkaline waving processes, and the nature of the invention as described below, the present process is effective in combination with acid and alkaline waving processes alike.

The present invention is an improvement in the acid or alkaline waving of human hair which enables simultaneous waving and dyeing of the hair. More particularly, in the process of waving hair with a reforming solution and rebonding the hair with an oxidizing rebonding agent, the present invention is the improvement comprising contacting the hair with a dye or tint after the reforming solution has been removed from the hair but before the oxidation rebonding is complete. In addition, the improvement preferably comprises admixing a tint or dye into all or a portion of the oxidizing rebonding agent (rebonding solution) to enable the application of most or all of the rebonding agent and all of the dye or tint to the hair simultaneously.

Waving and dyeing carried out by the present procedure have consistently produced both effective permanent waves and satisfactory tints, whereas if the dye and the reforming solution contact the hair simultaneously, little or no effect is obtained from the dye. In theory, although applicant does not wish to be bound by this theory, applicant believes that, in the latter case, the action of the reforming solution in penetrating and "opening up" the hair cuticle also permits the tint or dye to escape back out through the cuticle of the hair as the reforming solution is rinsed or removed. In accordance with the present invention, therefore, the dye or tint is not applied to the hair until after the reforming solution is removed from the hair. Hair waved and tinted in accordance with the invention accordingly demonstrates the desired tint along with a satisfactory permanent wave.

In accordance with the preferred embodiment of the invention, therefore, the single process perm and tint proceeds as follows. The hair is first shampooed, after which it is then wound onto rods in accordance with permanent waving techniques known in the art. After winding, the hair is saturated with between 40 and 100 ml. of a reforming solution. The reforming solutions suitable for the practice of the invention are known in the art and ordinarily contain at least one mercaptan acid selected from the group including, but not limited to, thioglycolic acid and the sodium, calcium and ammonium salts thereof, 2,5-dimercaptothiodiazoline, thiosuccinic acid and derivatives thereof, thiolactic acid and derivatives thereof and thiophenol and derivatives thereof. The mercaptan acid is present in the reforming solution in amounts known in the art, and furthermore generally is present in an amount between about 1 and 7 percent by weight in an aqueous solution; the reforming solution may also contain conditioners known in the art. More preferably, the mercaptan acid is thioglycolic acid, which is present in the reforming solution in an amount between about 3 and 5 percent by weight and which is unaccompanied by ammonium hydroxide or other alkali. Mild heat is then applied to the hair by, for example, covering the hair with a vapor barrier such as a plastic cap and permitting the body heat near the scalp to heat the lotion-soaked hair. The hair is subjected to mild heat for 2 to 25 minutes depending on the hair type. The reforming solution is then rinsed or thoroughly blotted from the hair.

Further in accordance with the preferred embodiment of the invention, the hair is then contacted with a rebonding solution or lotion, containing at least one oxidizing compound selected from the group including, but not limited to, oxygen, hydrogen, peroxide, bromate, or bromite, or combinations thereof, to which has been added immediately before application the desired amount of hair tint or dye. The oxidizing compound is present in an amount between about 0.2 and 10 percent by weight of the oxidizing rebonding agent. Suitable dyes or tints (dyeing compositions) include, but are not limited to, compositions containing paraphenylenediamine, 5-methoxy paraphenylenediamine, 2,6-dimethyl-3-methoxy paraphenylenediamine, 2,6-dimethyl paraphenylenediamine, 4-amino-N,N-dihydroxyethyl aniline, 4-amino-N-ethyl-N-carbamylmethyl aniline, paraaminophenol, 2-methyl-4-amino phenol, 3-chloro-4-amino phenol, 1-amino-N,N-dihydroxyethyl-3-nitro-4-amino-N' methyl benzene, 1-amino-N,N,methyl-hydroxyethyl-3-nitro-4-amino-N'-hydroxyethyl benzene, 1-amino-N,N-methyl-hydroxyethyl-3-nitro-4-amino-N'-methyl benzene, 3-nitro-4-amino-N-hydroxyethyl anisole, 3-nitro-4-amino-N-hydroxyethyl phenol, (3-nitro-4-amino)phenoxyethanol, (3-nitro-4-amino-N-methyl)phenoxyethanol, 2-hydroxyethylamino-5-nitro anisole, 2-methyl-4-nitro aniline, 4,4'-dihydroxy-2-amino-5-methyl diphenylamine, 4,4'-dihydroxy-2-amino-N-hydroxyethyl-5-methyl-2'-chloro diphenylamine, 2,4'-diamino-4-hydroxy-5-methyl-diphenylamine, anthraquinone compounds, azo compounds including 2,2'-di-aminoazobenzene, 4,4'diaminoazobenzene, 2,4'diaminoazobenzene, 4-amino-4'N'hydroxyethyl-aminoazobenzene, 4,4'-diaminophenylazonaphthalene, 4-amino-4'-dimethyl aminoazobenzene, and inorganic and organic metal salts.

The dyeing composition is ordinarily added to a rebonding solution which is chemically compatible with the formulation of the dye or tint. Furthermore, in view of the widespread use of oxidizing agent-activated dyeing compositions such as paraphenylenediamines, the oxidizing rebonding agent is preferably admixed with an oxidizing agent-activated dyeing composition in order to maximize the utility of the oxidizing agent. For example, a hydrogen peroxide containing rebonding agent may be admixed with a peroxide-activated dyeing composition (along with added alkali, if necessary, to correct the pH as suggested by the manufacturer of the dye). The oxidizing agent present in the admixture, therefore, functions both as a rebonding agent and as an activator for the dyeing composition. For this reason, whereas two applications of an oxidizing agent are required when tinting and waving are performed separately, the use of an oxidizing rebonding agent/dye admixture minimizes damage to the hair because a single application of the oxidizing agent accomplishes both rebonding and dye activation.

The concentration of the dyeing composition within the rebonding agent/dye admixture should approximate the concentration of the diluted dye as ordinarily applied to the hair. Equivalent amounts of dye may, of course, be used in higher concentrations per smaller total volume. Actual concentrations for any given dyeing composition may be readily determined from the instructions provided by the manufacturer of the dye, and will generally range between 0.5 and 10 percent by weight of the total rebonding agent/dye admixture.

Further in accordance with the preferred embodiment of the invention, between about 40 and about 160 ml. of the oxidizing rebonding agent/dye admixture is applied evenly to the hair and is permitted to remain on the hair for approximately 5 minutes, depending on hair type. The rods are then carefully removed from the hair and the hair is massaged gently to disperse the dyeing composition evenly over the entire shaft of each hair. After the rods are removed, the rebonding agent/dye admixture is left in place for approximately 5 minutes on virgin (not previously tinted) hair and for approximately 3 minutes on previously tinted hair. After rebonding and tinting are complete, the oxidizing rebonding agent/dye admixture is thoroughly rinsed from the hair. The hair may then be styled and dried as desired.

In an alternate embodiment of the invention, an alkaline reforming solution is substituted for the acid reforming solution of the present invention. The present process proceeds as with the preferred embodiment, except that no application of mild heat to the hair is required at any time during the procedure.

In another alternate embodiment of the invention, the dyeing composition is added to only a portion of the oxidizing rebonding agent. This alternate embodiment of the invention is useful in adapting the invention for use with thick dyeing compositions, compositions which were thickened during the manufacturing process to ensure dripless application. Applicant has observed that, with these thickened dyes, superior results are obtained by contacting the hair (still wound on the rods) with a portion of the oxidizing rebonding agent alone, followed by the application of the remainder of the oxidizing rebonding agent admixed with the desired amount of dye. The rebonding process is then completed in accordance with the preferred embodiment of the invention.

In a further alternate embodiment of the invention, the dyeing composition need not be admixed with the oxidizing rebonding agent at all but may be applied before or during the application of the rebonding agent to the hair. For example, the paraphenylenediamine dyes discussed above may be applied before or during the application of the oxidizing rebonding agent; the presence of the rebonding agent will chemically activate the dye in the same way as if the dye and the rebonding agent had first been admixed.

A number of modifications may be made to the process described above without affecting the nature or scope of the present invention. For example, although the oxidizing rebonding agent is preferably a liquid, gaseous oxidizing rebonding agents may be employed in the present invention. Likewise, reforming solutions other than mercaptan acid solutions may be used to reform the hair as long as the reforming step is followed by a rebonding procedure which takes place during or after the application of the dye or tint. In addition, any of the solutions or lotions may be supplemented with hair conditioners known in the art. Furthermore, although for convenience the applicant has used the term "permanent wave" for its clarity as generally used, the present process may also be used with hair straightening or curl relaxing procedures which employ a mercaptan acid or other reforming solution followed by the application of a bonding agent. Accordingly, by the term permanent waving, applicant intends to signify the permanent reconfiguring of the hair. As a result, although in the preferred embodiment the hair is wrapped onto rods, additional hair configuring means such as wrappers, clamps, clips, plates, pulls and weights may be used in place of the waving rods as described. In addition, hair other than human hair may be dyed and reconfigured according to the present process. For these and other reasons, although the invention has been described with reference to specific materials and specific methods, it is only to be limited so far as is set forth in the accompanying claims.

The invention will be further illustrated by the following examples.

EXAMPLE I

A reforming solution was selected which contained 5 percent sodium thioglycolate by weight and 3 percent hydrolyzed collagen protein conditioner by weight, along with sufficient water to yield 50 mls. of reforming solution. The hair of a test subject was shampooed and thoroughly squeezed with an absorbent towel. The hair was subsequently rolled onto permanent waving rods and the hair on the rods was then saturated with the reforming solution. A plastic cap was positioned over all the lotion-soaked rods and the test subject was left undisturbed for 20 minutes.

After a test curl indicated a proper degree of reformation, the test curl was rewound onto the rod, the rods were rinsed with lukewarm tap water for 5 minutes, and the hair was blotted dry with a soft towel.

A solution was admixed containing 3 percent by weight hydrogen peroxide in water, along with 4 percent by weight of a paraphenylenediamine dye admixture formulated to give a deep auburn tint to the hair upon application in the presence of peroxide. Sufficient water was added to yield a total volume of 100 mls. of the admixture. The admixture was gently swirled in a cylindrical plastic flask to mix, a thin-stream dispenser was affixed thereto, and the dye/peroxide admixture was dispensed evenly over all of the rods. The admixture was left in place for 5 minutes, after which the rods were carefully removed from the hair and the hair was gently massaged to spread the rebonding agent/dye admixture evenly throughout the hair. Because the hair had been previously tinted, the admixture was left in place for only 3 minutes after removal of the rods. After 3 minutes, the hair was thoroughly rinsed in lukewarm water and styled by methods known in the art.

EXAMPLE II

The process according to the present invention was carried out in accordance with Example I, except that the reforming solution contained sufficient sodium hydroxide to result in an alkaline pH of the reforming solution as a whole, and no plastic cap was positioned over the reforming solution-soaked rods.

EXAMPLE III

The reformation stage of the present invention was carried out in accordance with Example I. A four ounce applicator bottle of a commercially available rebonding agent, which contained 3 percent hydrogen peroxide, was selected for use. One ounce of the rebonding agent was transferred to a second applicator bottle and about 1½ ounces of a thickened commercially available dyeing preparation was added to the first applicator bottle. The bottle was shaken gently. The one ounce of plain rebonding agent was applied to the hair followed by the contents of the second applicator bottle. As a result, approximately 1 oz. of the rebonding agent was applied to the rods prior to the application and even distribution of the remaining 3 oz. portion of 3 percent hydrogen peroxide admixed with all of the dyeing composition. Rebonding was then completed in accordance with Example I. The sequential application of the two portions of the rebonding agent gave a satisfactory permanent wave and a tint of the desired shade.

I claim:

1. In the process of permanently waving hair with a reforming solution, removing said reforming solution and rebonding said hair by saturating said hair with an oxidizing rebonding agent and subsequently removing said rebonding agent, the improvement comprising contacting said hair with a dyeing composition after said reforming solution is removed from said hair but before said rebonding agent is removed from said hair.

2. In the process according to claim 1, the improvement further comprising contacting said hair with a dyeing composition while said hair is saturated with an oxidizing rebonding agent.

3. In the process according to claim 1, the improvement further comprising contacting said hair with a dyeing composition before said rebonding agent is applied to said hair.

4. In the process according to claim 1, the improvement further comprising contacting said hair with an admixture containing a dyeing composition and an oxidizing rebonding agent after said reforming solution is removed from said hair.

5. In the process according to claim 4, the improvement further comprising contacting said hair with an admixture comprising a dyeing composition and an oxidizing rebonding agent containing a compound selected from the group consisting of oxygen, hydrogen, peroxide, bromate, or bromite, after said reforming solution is removed from said hair.

6. In the process according to claim 4, the improvement further comprising contacting said hair with an admixture containing a paraphenylenediamine dye and a peroxide after said reforming solution is removed from said hair.

7. A rebonding agent composition comprising an admixture of a dyeing composition and an oxidizing rebonding agent.

8. The rebonding agent composition of claim 7 wherein said dyeing composition is selected from the group consisting of paraphenylenediamine dyes, paraaminophenol dyes, anthraquinone dyes or diaminoazobenzene dyes.

9. The rebonding agent composition of claim 8 wherein said oxidizing rebonding agent includes a compound selected from the group consisting of oxygen, hydrogen, peroxide, bromate, or bromite.

10. The rebonding agent composition of claim 9 wherein said oxidizing rebonding agent includes a peroxide and wherein said dyeing composition is a paraphenylenediamine dye.

11. The rebonding agent composition of claim 10 wherein said peroxide is hydrogen peroxide.

* * * * *